US010179031B2

(12) United States Patent
Haimerl et al.

(10) Patent No.: US 10,179,031 B2
(45) Date of Patent: Jan. 15, 2019

(54) INTERRELATED POINT ACQUISITION FOR NAVIGATED SURGERY

(71) Applicant: Brainlab AG, Munich (DE)

(72) Inventors: Martin Haimerl, Gilching (DE); Mario Schubert, Poing (DE)

(73) Assignee: Brainlab AG, Munich (DE)

( * ) Notice: Subject to any disclaimer, the term of this patent is extended or adjusted under 35 U.S.C. 154(b) by 339 days.

(21) Appl. No.: 15/027,606

(22) PCT Filed: Oct. 28, 2013

(86) PCT No.: PCT/EP2013/072498
§ 371 (c)(1),
(2) Date: Apr. 6, 2016

(87) PCT Pub. No.: WO2015/062621
PCT Pub. Date: May 7, 2015

(65) Prior Publication Data
US 2016/0249985 A1  Sep. 1, 2016

(51) Int. Cl.
*G06F 17/30* (2006.01)
*A61B 34/20* (2016.01)
(Continued)

(52) U.S. Cl.
CPC ............. *A61B 34/20* (2016.02); *G06F 19/00* (2013.01); *G06F 19/324* (2013.01); *G16H 40/63* (2018.01);
(Continued)

(58) Field of Classification Search
USPC ........ 707/608, 609, 687, 705, 790, 813, 821
See application file for complete search history.

(56) References Cited

U.S. PATENT DOCUMENTS 6,096,050 A     8/2000  Audette
8,447,085 B2 *  5/2013  Gloger .................... G06T 7/187
                                                         382/128
(Continued)

FOREIGN PATENT DOCUMENTS

EP      1923015 A1      5/2008
WO   2012171577 A1     12/2012

OTHER PUBLICATIONS

International Preliminary Report on Patentability, PCT/EP2013/072498 filed on Oct. 28, 2013, pp. 1-5, dated May 3, 2016; The International Bureau of WIPO, Switzerland.
(Continued)

*Primary Examiner* — Sana A Al-Hashemi
(74) *Attorney, Agent, or Firm* — Tucker Ellis LLP

(57) ABSTRACT

The present invention relates to a method for acquiring the position of points for navigated surgery, the method being constituted to be executed by a computer and comprising the following steps:—acquiring, on the basis of detecting a first tracked device, first point position data for each of at least two points, wherein the first point position data comprise point position information describing the three-dimensional position of the point within a first co-ordinate system assigned to the first tracked device;—acquiring first co-ordinate transformation data for each of at least two points, wherein the first co-ordinate transformation data comprise co-ordinate transformation information describing a transformation of the three-dimensional position of the point from the first co-ordinate system to a second co-ordinate system;—acquiring second co-ordinate transformation data for each of at least two points, wherein the second co-ordinate transformation data comprise co-ordinate transformation information describing a transformation of the three-dimensional position of the point from the second co-ordinate system to a third co-ordinate system assigned to
(Continued)

Figure 1:
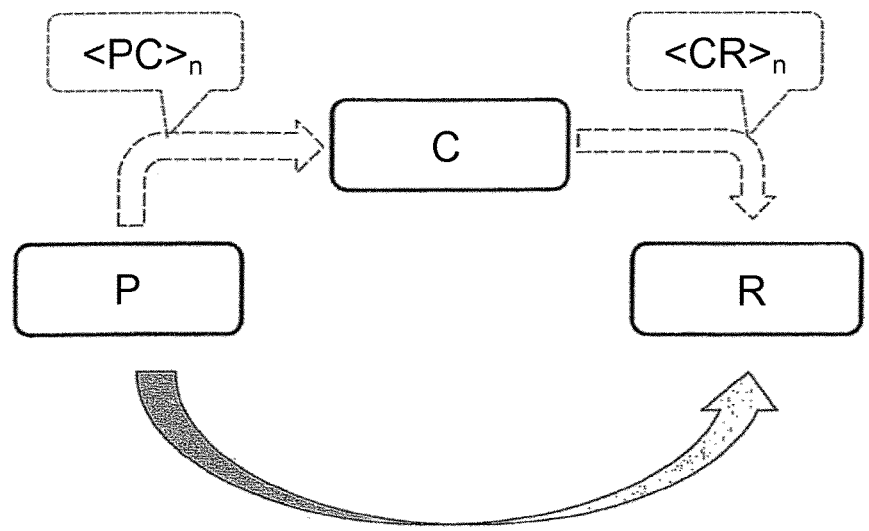

a second tracked device;—determining, on the basis of the first and second co-ordinate transformation data, second point position data for each of at least two points, wherein the second point position data comprise point position information describing the three-dimensional position of the point within the third co-ordinate system; wherein the second point position data of at least one of the at least two points are determined on the basis of the second co-ordinate transformation data of at least one other of the at least two points.

11 Claims, 1 Drawing Sheet

(51) Int. Cl.
*G06F 19/00* (2018.01)
*G16H 40/63* (2018.01)
*A61B 90/00* (2016.01)
(52) U.S. Cl.
CPC . *A61B 2034/2068* (2016.02); *A61B 2090/363* (2016.02); *A61B 2090/364* (2016.02)

(56) References Cited

U.S. PATENT DOCUMENTS

| | | | |
|---|---|---|---|
| 2007/0100880 A1* | 5/2007 | Buscema | G06F 17/10 |
| 2007/0110290 A1* | 5/2007 | Chang | G06T 5/001 |
| | | | 382/128 |
| 2008/0008399 A1* | 1/2008 | Marugame | G06T 17/10 |
| | | | 382/285 |
| 2008/0154125 A1 | 6/2008 | Maier et al. | |
| 2012/0330135 A1 | 12/2012 | Millahn et al. | |
| 2014/0270164 A1* | 9/2014 | Aggarwal | H04L 9/0816 |
| | | | 380/46 |

OTHER PUBLICATIONS

International Search Report,PCT/EP2013/072498 filed on Oct. 28, 2013, pp. 1-3, dated Aug. 1, 2014, European Patent Office, Netherlands.

\* cited by examiner

INTERRELATED POINT ACQUISITION FOR NAVIGATED SURGERY

RELATED APPLICATION DATA

This application is a national phase application of International Application No. PCT/EP2013/072498 filed Oct. 28, 2013 and published in the English language.

The present invention relates to a computer-implemented method for acquiring the position of points for navigated surgery. It also relates to a corresponding program, a corresponding computer, a corresponding program storage medium and a corresponding signal wave provided for performing such a method.

Usually, intra-operative point acquisition for navigated surgery is performed in relation to a marker array which is reliably fixed to an anatomical structure. As long as there is a consistently stable and accurate relationship between the marker array and the anatomical structure, inaccuracies in acquiring the position of the points remain within acceptable limits. However, when a marker array is not fixed sufficiently securely to the structure and/or is far away from the region of interest, the tracking accuracy can be compromised in the region of interest.

EP 1 923 015 A1 discloses a method for determining whether or not a reference array moves within the surgical environment.

WO 2012/171577 discloses a commonly performed cup-verification workflow which is known from the prior art and described in more detail further below.

It is the object of the present invention to increase the accuracy of point acquisition procedures. This object is achieved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention provides a method for acquiring the position of points for navigated surgery, the method being constituted to be executed by a computer and comprising the following steps:
  acquiring, on the basis of detecting a first tracked device, first point position data for each of at least two points, wherein the first point position data comprise point position information describing the three-dimensional position of the point within a first co-ordinate system assigned to the first tracked device;
  acquiring first co-ordinate transformation data for each of at least two points, wherein the first co-ordinate transformation data comprise co-ordinate transformation information describing a transformation of the three-dimensional position of the point from the first co-ordinate system to a second co-ordinate system;
  acquiring second co-ordinate transformation data for each of at least two points, wherein the second co-ordinate transformation data comprise co-ordinate transformation information describing a transformation of the three-dimensional position of the point from the second co-ordinate system to a third co-ordinate system assigned to a second tracked device;
  determining, on the basis of the first and second co-ordinate transformation data, second point position data for each of at least two points, wherein the second point position data comprise point position information describing the three-dimensional position of the point within the third co-ordinate system;
wherein the second point position data of at least one of the at least two points are determined on the basis of the second co-ordinate transformation data of at least one other of the at least two points.

In other words, the present invention provides a method by means of which the position of at least two points is acquired. These points can be landmarks or other points of interest, the position of which is to be determined in three-dimensional space. Normally, a pointer instrument which is tracked by a surgical navigation system is used as a first tracked device to palpate these points or landmarks, such that the position of the palpated points is known with respect to the co-ordinate system assigned to the first tracked device (the pointer). Alternatively or even additionally (as a redundant system), such a tracked device or pointer can in turn be "tracked" by a system comprising at least one gyro-sensor and/or inertia sensor which is attached to the device and determines the spatial position of the tracked device or pointer.

In known point acquisition methods, the three-dimensional co-ordinates within the co-ordinate system assigned to the pointer are transferred, separately for each palpated point, to the co-ordinate system assigned to a second tracked device which is fixedly attached to the anatomical structure comprising the palpated points. This allows the anatomical structure and the palpated points to be tracked in three-dimensional space by tracking the second tracked device by means of the tracking system.

However, registration often requires points outside the treated area of a patient to be acquired. These points are acquired at a significantly lower level of accuracy, because the points are further away from the reference array attached to the anatomical structure. In addition, surgical instruments such as cup inserters which can be used as the second tracked device often have a smaller marker geometry in order to avoid conflicts with soft-tissue structures, which further reduces the accuracy in point acquisition which can be achieved. In addition, the fixing connection between surgical instruments such as cup inserters and anatomical structures of a patient almost always exhibits a certain flexibility, such that it cannot be guaranteed that the instrument is connected sufficiently fixedly to the anatomical structure.

The present invention uses a first co-ordinate transformation to transfer the point co-ordinates for each palpated point from the co-ordinate system assigned to the first tracked device (the pointer) to a second co-ordinate system which does not change its position within the surgical operating area, i.e. which is globally fixed, at least during the time required to determine the position of each of the points within the third co-ordinate system. The co-ordinates for each palpated point are then transferred from the second, globally fixed co-ordinate system to a third co-ordinate system which is assigned to the tracked device attached to the anatomical structure. In accordance with the present invention, however, the co-ordinate transformation for at least one point from the second co-ordinate system to the third co-ordinate system also takes into account the transformation of the co-ordinates of at least one other palpated point from the second co-ordinate system to the third co-ordinate system.

The method of the invention can in particular be used in connection with hip navigation surgery, wherein a cup implant is inserted and fixed into an acetabular cavity, while a navigated cup inserter (the second tracked device) is still attached to the implant and tracked by a tracking system. A registration procedure can then be performed in relation to the marker array fixed to the cup inserter, such that all the required landmark information can be acquired in relation to the co-ordinate system provided by the cup inserter marker array. For this purpose, the position of the cup inserter needs to be completely fixed in relation to the pelvic bone, and the relative position of the anatomical structure/point and the camera has to be stable during and between the point acquisitions which are taken into account, such that there is no significant variation between the point positions according to the camera co-ordinates and the point positions of the palpated points of the anatomical structure.

In accordance with a preferred embodiment of the present invention, the second co-ordinate system—which is spatially invariant relative to the surgical operating area, at least during the time required to determine the position of each of the points within the third co-ordinate system—is a co-ordinate system assigned to the camera array of the medical tracking system. The camera array of a medical tracking system usually remains stable during a surgical procedure, such that its co-ordinate system can be used to perform the method of the invention. The second co-ordinate transformation data for at least one of the two points can also be stored on suitable means, such that these data can be subsequently taken into account when the co-ordinates for each of the palpated points are to be transferred from the second co-ordinate system (the camera co-ordinate system) to the third co-ordinate system assigned to the second tracked device (the cup inserter).

The method of the invention can also comprise the step of determining possible differences in the second co-ordinate transformation data for at least two of the at least two points, so as to ensure that the anatomical structure does not move relative to the camera co-ordinate system while the point positions of landmarks are being determined by palpating them with the tracked pointer. The relative position between the camera and the cup inserter marker array is thus checked between point acquisition steps.

In accordance with another preferred embodiment of the present invention, the method comprises the step of determining mean second co-ordinate transformation data if any differences in the second co-ordinate transformation data are found, wherein the mean second co-ordinate transformation data are determined on the basis of second co-ordinate transformation data for at least two of the at least two points, and wherein the second point position data are then determined on the basis of the mean second co-ordinate transformation data. It is thus possible to compensate for any differences caused for example by tracking inaccuracies, such that the overall accuracy in determining the position of each point within the third co-ordinate system can be increased. The mean second co-ordinate transformation data can also be determined on the basis of mathematical algorithms used to compensate for the error influences which cause said differences.

It is generally possible to use the positional information of the cup inserter marker array to average the co-ordinate information, so as to improve the overall accuracy. It is also possible to use an average value, which is derived for each point from the acquired position of one or more preceding points.

It is also possible to determine the second point position data for one or more of the acquired points on the basis of a combination of the point position relative to the third co-ordinate system and the point position relative to the second co-ordinate system.

The method according to the present invention can also comprise the step of evaluating, on the basis of the determined differences in the second co-ordinate transformation data for at least two of the at least two points, possible changes in the position of the third co-ordinate system relative to the second co-ordinate system during the point position acquisition procedure. In other words, the information from the marker array can be used to check whether there was any movement in the position of the anatomical structure in relation to the camera co-ordinate system. Such movements can be detected when significant changes in the position of the marker array occur during the point acquisition procedure for two or more points. Using this technique, an instrument can be tracked in the camera co-ordinate system until a significant deviation in the relative position between the camera co-ordinate system and the co-ordinate system of the marker array attached to the anatomical structure is detected.

In accordance with another preferred embodiment of the present invention, the method comprises at least one of the steps of:
  determining at least one outlying second co-ordinate transformation on the basis of a comparison of second co-ordinate transformation data for at least three points;
  weighting the at least one outlying second co-ordinate transformation or replacing it with a different second co-ordinate transformation, in particular the mean second co-ordinate transformation or a second co-ordinate transformation for at least one other point;
  indicating that a point position acquisition procedure is to be repeated for at least the point exhibiting the outlying second co-ordinate transformation.

Outlying co-ordinate transformations, i.e. ones which differ significantly from the majority of other corresponding co-ordinate transformations, can be underlying factors for certain errors, which can therefore be detected using such an approach.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The present invention is also directed to a navigation system for computer-assisted surgery. This navigation system preferably comprises the aforementioned computer for processing the data provided in accordance with the data processing method as described in any one of the preceding embodiments.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument).

In the following, definitions are provided for some of the relevant terms used within this application.

For this purposes of this document, a computer is a technical computer which in particular comprises technical, in particular tangible components, in particular mechanical and/or electronic components. Any device mentioned as such in this document is a technical and in particular tangible device.

It is the function of a reference array comprising several markers to be detected by a marker detection device (for example, a camera array or an ultrasound receiver or analytical devices such as CT or MRI) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has an at least substantially spherical shape, and can therefore be referred to as a marker sphere, or a circular shape and can therefore be referred to as a marker disc; markers can however also exhibit a cornered, for example cuboid, shape.

A marker array or reference array can for example be a reference star or a pointer or a single marker or a plurality of (individual) markers which are then preferably in a predetermined spatial relationship. A marker array comprises one, two, three or more markers, wherein two or more such markers are in a predetermined spatial relationship. This predetermined spatial relationship is in particular known to a navigation system and is for example stored in a computer of the navigation system.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star in particular features a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Another example of a landmark is one defined by the rim of the acetabulum or any other significant feature of the acetabulum, such as for example the centre of the acetabulum. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the centre of rotation of the femur when moved relative to the acetabulum.

A detection point is in particular a point on the surface of the anatomical structure which is detected, for example by a pointer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the following, the invention is described with reference to the figures which represent preferred embodiments of the invention, without limiting the invention to the specific features shown in the figures.

FIG. 1 schematically shows a method for acquiring the position of points for navigated surgery, such as is usually performed in accordance with the prior art.

Figure 2:
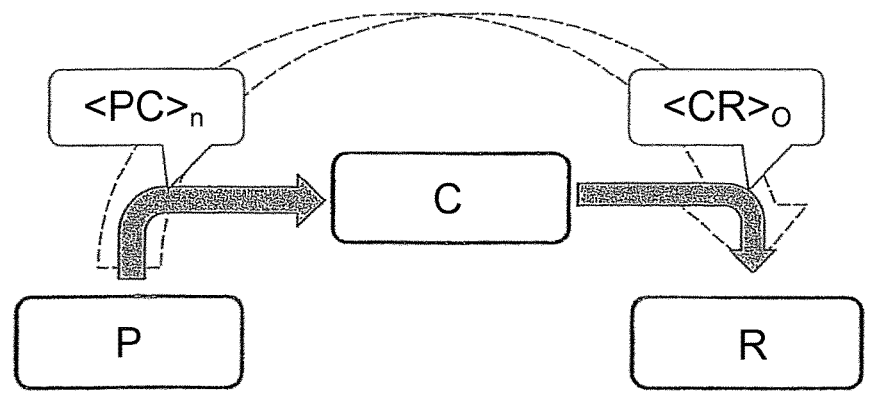

FIG. 2 schematically shows a method for acquiring the position of points for navigated surgery in accordance with the present invention.

In accordance with the prior-art method as shown in FIG. 1, the co-ordinates of each point or landmark palpated by a tracked pointer are acquired in the co-ordinate system P which is assigned to a pointer instrument. For each palpated point n, a transformation matrix $<PC>_n$ is acquired for transferring the point co-ordinates from the co-ordinate system P assigned to the pointer to a co-ordinate system C which is assigned to a camera array of the tracking system. A transformation matrix $<CR>_n$ is then acquired, separately for each palpated point, for transferring the point co-ordinates from the co-ordinate system C assigned to the camera array to a co-ordinate system R which is assigned to a reference array which is fixedly attached to the anatomical structure on which the palpated points or landmarks are palpated. In the prior art, every point acquisition is considered separately, and the position of every point is transferred from the co-ordinate system P to the co-ordinate system R by means of the transformation matrices $<PC>_n$ and $<CR>_n$.

In accordance with a preferred embodiment of the present invention as shown in FIG. 2, however, point acquisition is not performed separately for each point. During point acquisition, each of the transformation matrices $<PC>_n$ and $<CR>_n$ is stored, wherein a single common overall matrix $<CR>_O$ is calculated on the basis of the plurality of the matrices $<CR>_n$ and then used to transfer the co-ordinates of all the palpated points from the co-ordinate system C to the co-ordinate system R. All the point co-ordinates within the co-ordinate system R can then be calculated, providing that the relative position and orientation of the camera and the reference array (the second co-ordinate system and the third co-ordinate system) has not changed during the time taken for all the point acquisitions. If any deviations do occur, measures can then be taken to compensate for the error influences, as already described further above.

The invention claimed is:

1. A data processing system, comprising a computer having a processor configured to execute a computer-implemented medical method for acquiring the position of points for navigated surgery, the method comprising the following steps:

acquiring, at the processor and on the basis of detecting a first tracked device, first point position data for each of at least two points, wherein the first point position data comprise point position information describing a three-dimensional position of the at least two points within a first co-ordinate system assigned to the first tracked device;

acquiring, at the processor, first co-ordinate transformation data for each of the at least two points, wherein the first co-ordinate transformation data comprise co-ordinate transformation information describing a transformation of the three-dimensional position of the at least two points from the first co-ordinate system to a second co-ordinate system assigned to a camera array of a medical tracking system which remains spatially invariant relative to a surgical operating area;

acquiring, at the processor, second co-ordinate transformation data for each of the at least two points, wherein the second co-ordinate transformation data comprise co-ordinate transformation information describing a transformation of the three-dimensional position of the at least two points from the second co-ordinate system to a third co-ordinate system assigned to a second tracked device attached to an anatomical structure comprising the at least two points;

determining, by the processor and on the basis of the first and second co-ordinate transformation data, second point position data for each of the at least two points, wherein the second point position data comprise point position information describing the three-dimensional position of the at least two points within the third co-ordinate system, wherein a common transformation matrix is calculated from the second co-ordinate transformation data for transferring the three-dimensional positions of all of the at least two points from the second co-ordinate system to the third co-ordinate system, and wherein the three-dimensional position of the at least two points within the third co-ordinate system is taken as a basis for a registration procedure for registering the anatomical structure with a medical image dataset, and/or for tracking procedure for tracking the spatial position of the anatomical structure within the three-dimensional space of the surgical operating area.

2. A computer-implemented medical method for acquiring the position of points for navigated surgery, the method comprising executing, on a processor of a computer, the steps of:

acquiring, at the processor and on the basis of detecting a first tracked device, first point position data for each of at least two points, wherein the first point position data comprise point position information describing a three-dimensional position of the point within a first co-ordinate system assigned to the first tracked device;

acquiring, at the processor, first co-ordinate transformation data for each of at least two points, wherein the first co-ordinate transformation data comprise co-ordinate transformation information describing a transformation of the three-dimensional position of the point from the first co-ordinate system to a second co-ordinate system;

acquiring, at the processor, second co-ordinate transformation data for each of at least two points, wherein the second co-ordinate transformation data comprise co-ordinate transformation information describing a transformation of the three-dimensional position of the point from the second co-ordinate system to a third co-ordinate system assigned to a second tracked device; and determining, by the processor and on the basis of the first and second co-ordinate transformation data, second point position data for each of at least two points, wherein the second point position data comprise point position information describing the three-dimensional position of the point within the third co-ordinate system, wherein the second point position data of at least one of the at least two points are determined on the basis of the second co-ordinate transformation data of at least one other of the at least two points.

3. A non-transitory computer-readable program storage-medium storing a computer program which, when executed on a processor of a computer or loaded into the memory of a computer, causes the computer to perform a computer-implemented medical method for acquiring the position of points for navigated surgery, the method comprising the following steps:

acquiring, at the processor and on the basis of detecting a first tracked device, first point position data for each of at least two points, wherein the first point position data comprise point position information describing a three-dimensional position of the point within a first co-ordinate system assigned to the first tracked device;

acquiring, at the processor, first co-ordinate transformation data for each of at least two points, wherein the first co-ordinate transformation data comprise co-ordinate transformation information describing a transformation of the three-dimensional position of the point from the first co-ordinate system to a second co-ordinate system;

acquiring, at the processor, second co-ordinate transformation data for each of at least two points, wherein the second co-ordinate transformation data comprise co-ordinate transformation information describing a transformation of the three-dimensional position of the point from the second co-ordinate system to a third co-ordinate system assigned to a second tracked device; and determining, by the processor and on the basis of the first and second co-ordinate transformation data, second point position data for each of at least two points, wherein the second point position data comprise point position information describing the three-dimensional position of the point within the third co-ordinate system, wherein the second point position data of at least one of the at least two points are determined on the basis of the second co-ordinate transformation data of at least one other of the at least two points.

4. The method according to claim 2, wherein the second co-ordinate transformation data for at least one of the at least two points are stored.

5. The method according to claim 2, wherein the second co-ordinate system is spatially invariant relative to a surgical operating area, at least during the time required to determine the position of each of the points within the third co-ordinate system, and is a co-ordinate system assigned to a camera array of a medical tracking system.

6. The method according to claim 2, further comprising the step of determining, by the processor possible differences in the second co-ordinate transformation data for at least two of the at least two points.

7. The method according to claim 2, further comprising the step of determining mean second co-ordinate transformation data if any differences in the second co-ordinate transformation data are found, wherein the mean second co-ordinate transformation data are determined on the basis of second co-ordinate transformation data for at least two of the at least two points, and wherein the second point position data are determined on the basis of the mean second co-ordinate transformation data.

8. A computer comprising the non-transitory computer-readable program storage medium according to claim 3.

9. The method according to claim 6, further comprising the step of evaluating, by the processor and on the basis of the determined differences in the second co-ordinate transformation data for at least two of the at least two points, possible changes in the position of the third co-ordinate system relative to the second co-ordinate system during the point position acquisition procedure.

10. The method according to claim 6, further comprising at least one of the steps of:

determining, by the processor, at least one outlying second co-ordinate transformation on the basis of a comparison of second co-ordinate transformation data for at least three points;

weighting, by the processor, the at least one outlying second co-ordinate transformation or replacing it with a different second co-ordinate transformation;

indicating, by the processor, that a point position acquisition procedure is to be repeated for at least the point exhibiting the outlying second co-ordinate transformation.

11. The method according to claim 7, wherein the mean second co-ordinate transformation data are determined on the basis of mathematical algorithms used to compensate for the error influences which cause said differences.

* * * * *